United States Patent
Miller et al.

(10) Patent No.: US 7,120,503 B2
(45) Date of Patent: Oct. 10, 2006

(54) STERILE DISPOSABLE INTERNAL DEFIBRILLATION PADDLES

(75) Inventors: James L. Miller, Westford, MA (US); Joan A. Kelly, Hampton, NH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 390 days.

(21) Appl. No.: 10/117,807

(22) Filed: Apr. 8, 2002

(65) Prior Publication Data

US 2003/0191501 A1    Oct. 9, 2003

(51) Int. Cl.
*A61N 1/04* (2006.01)
(52) U.S. Cl. .................................... 607/129
(58) Field of Classification Search ........... 607/116, 607/119, 129
See application file for complete search history.

(56) References Cited

U.S. PATENT DOCUMENTS

| | | | | |
|---|---|---|---|---|
| 2,985,172 A | * | 5/1961 | Jones | 607/119 |
| 3,196,877 A | * | 7/1965 | Corbin | 607/142 |
| 3,389,703 A | * | 6/1968 | Criswell et al. | 607/119 |
| 4,030,509 A | * | 6/1977 | Heilman et al. | 607/17 |
| 4,938,231 A | * | 7/1990 | Milijasevic et al. | 607/129 |
| 5,327,909 A | * | 7/1994 | Kiser et al. | 607/129 |
| 5,562,710 A | * | 10/1996 | Olsen et al. | 607/5 |
| 5,690,648 A | * | 11/1997 | Fogarty et al. | 606/129 |
| 2003/0083729 A1 | * | 5/2003 | Solosko et al. | 607/142 |
| 2003/0114885 A1 | * | 6/2003 | Nova et al. | 607/2 |

* cited by examiner

*Primary Examiner*—Robert E. Pezzuto
*Assistant Examiner*—Frances P. Oropeza
(74) *Attorney, Agent, or Firm*—Tony Piotrowski

(57) ABSTRACT

A disposable internal defibrillator paddle providing for a more economical and easier defibrillation procedure than non disposable paddles. The disposable paddle contains: (a) a handle attached to a shaft attached to a spoon, the spoon having a receiving unit, and the handle, the shaft, and the spoon are all made of non conducting material; and (b) an electrode plate attaching onto the receiving unit of the spoon.

23 Claims, 6 Drawing Sheets

STERILE DISPOSABLE INTERNAL DEFIBRILLATION PADDLES

BACKGROUND OF THE INVENTION

During open-heart surgery, a pair of internal defibrillation paddles is used to restart the patient's heart. Each internal defibrillation paddle comprises a handle attached to a shaft attached to a spoon electrode. The paddle handles are held by a surgeon while the spoon electrodes are inserted into the patient's chest and placed in direct contact with the myocardium (heart muscle). An electric discharge is passed from one spoon electrode through the patient's heart to a second spoon electrode.

Prior to use, paddle electrodes must be sterilized to eliminate patient infection. Modern sterilization methods use heat or chemical agents, such as ethylene oxide. The methods and materials used degrade the paddle materials limiting their useful life. Most manufacturers specify a maximum service life for paddles, usually in the range of 50–100 sterilization cycles. However, there is no convenient mechanism for users to measure and track the number of sterilization cycles a paddle experiences. Therefore, there is no easy way to determine if the service life of the paddles has been exceeded.

Sterilization can cause two problems. First, the process is expensive and often uses environmentally unfriendly materials. Second, it is destructive and the expensive reusable paddles must be replaces periodically. Furthermore, it is difficult to pass the cost of the paddle electrodes to the patient because the actual service life is indeterminate.

Paddle cleaning is required after use because dried blood and other dried body fluids must be removed prior to sterilization. Cleaning is time consuming, expensive, and hazardous due to possible contamination with AIDS, Hepatitis, or other infectious materials.

Further, paddles are now made as durable as possible. This means that a paddle electrode contact area is made of thick rigid metal in the shape of a large flat "spoon." This one-size fits all shape of the spoon is fixed and may not conform equally well to the curvature of all hearts.

Therefore, what is needed is a paddle not subject to the problems indicated above, such as a disposable paddle. What is also needed is a way to test the disposable paddle without comprising the sterility of the paddle.

SUMMARY OF THE INVENTION

In an exemplary embodiment, the present invention provides for disposable paddles that are economical to manufacture and require no cleaning or maintenance as non-disposable paddles do.

Furthermore, the present invention provides for disposable paddles in a sterile package capable of being tested without comprising the sterility of the paddles or the package.

Moreover, the present invention provides for a spoon electrode and shaft that are flexible allowing for custom shaping and better electrical contact potentially allowing reduced energy shocks.

Thus, objects of the present invention are to realize an improved internal defibrillation system. Objects of the present invention can be achieved, in one embodiment, by a self testing internal defibrillator package apparatus, which includes (a) a first spoon electrode inside the package, the first spoon electrode electrically connected to a first wire inside the package; (b) a second spoon electrode inside the package, the second spoon electrode electrically connected to a second wire inside the package; (c) a testing unit inside the package electrically connecting the first spoon electrode and the second spoon electrode; (d) a first conductor located outside the package, the first conductor electrically connected to the first wire; and (e) a second conductor located outside the package, the second conductor electrically connected to the second wire.

Objects of the invention can also be achieved, in one embodiment, by an apparatus which includes (a) a disposable paddle apparatus which includes a shaft; and (b) a malleable spoon electrode connected to the shaft, allowing an operator to contour the spoon electrode to a particular shape.

Objects of the invention can also be achieved, in one embodiment, by a method which includes (a) molding two malleable spoon electrodes to conform to a patient's heart; and (b) applying an electric charge between the spoon electrodes to attempt to resuscitate the heart.

Objects of the invention can also be achieved, in one embodiment, by an apparatus which includes (a) a first internal defibrillator paddle and a second internal defibrillator paddle both electrically connected to a testing unit, the paddles and the testing unit located inside a package; and (b) a first connector connected to the first internal defibrillator paddle and a second connector connected to the second internal defibrillator paddle, both connectors located outside of the package, wherein an electrical charge placed between the first connector and the second connector activates the testing unit.

Objects of the invention can also be achieved, in one embodiment, by an apparatus which includes (a) a handle attached to a shaft attached to a spoon, the spoon having a receiving unit, and the handle, the shaft, and the spoon are all made of non conducting material; and (b) an electrode plate attaching onto the receiving unit of the spoon.

Objects of the invention can also be achieved, in one embodiment, by an apparatus which includes (a) a nonconductive handle integrally attached to a nonconductive shaft integrally attached to a conductive spoon electrode, wherein the spoon electrode is made of a malleable material.

DESCRIPTION OF THE PREFERRED EMBODIMENTS

Figure 1:
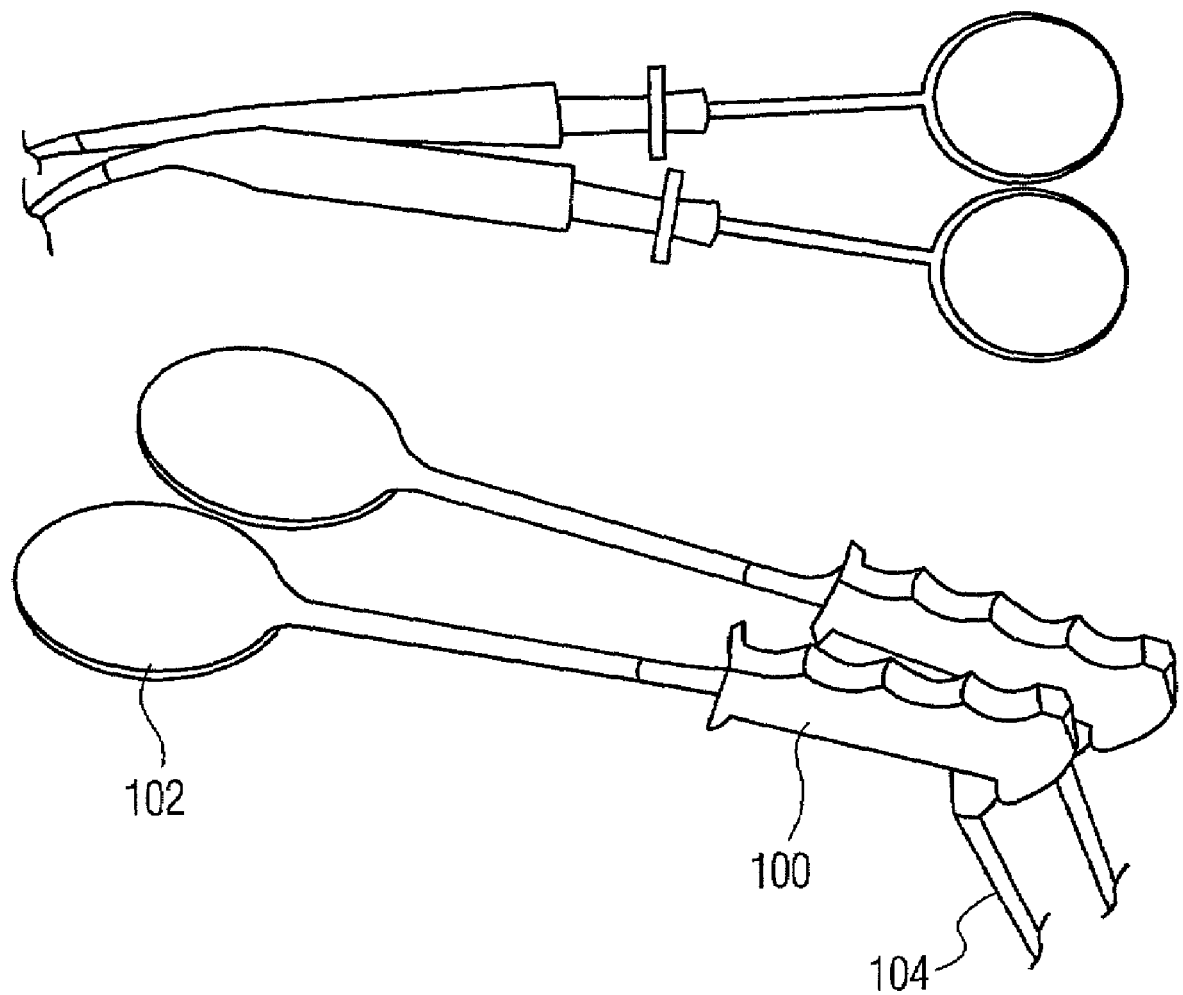
FIG. 1 is a drawing illustrating prior art paddles.

Reference will be now made in detail to the present preferred embodiments of the present invention, examples of which are illustrated in the accompanying drawings, wherein like reference numerals refer to the like elements throughout.

The present invention provides for disposable internal defibrillator paddles ("paddles"). Disposable paddles are preferable to standard reusable paddles in that no cleaning or re-sterilization is needed. Further, the present invention provides for sterile testing paddles, which do not compromise the sterility of the package. An electric charge can be placed on connectors located outside of the package, yet if the paddles operate properly, a visual indication will result.

FIG. 1 is a drawing illustrating prior art internal paddles. The paddles pictured are not disposable, nor are they specially packaged. The paddle comprises a handle 100 attached to a shaft 101 attached to a spoon electrode 102. Since theses paddle are not disposable, the spoon 102 must be rigid, and not capable of being shaped. A wire 104 should be connected to a power source. Paddles like this are used in pairs, with an electric current generated between them to help start a patient's heart.

Figure 2:
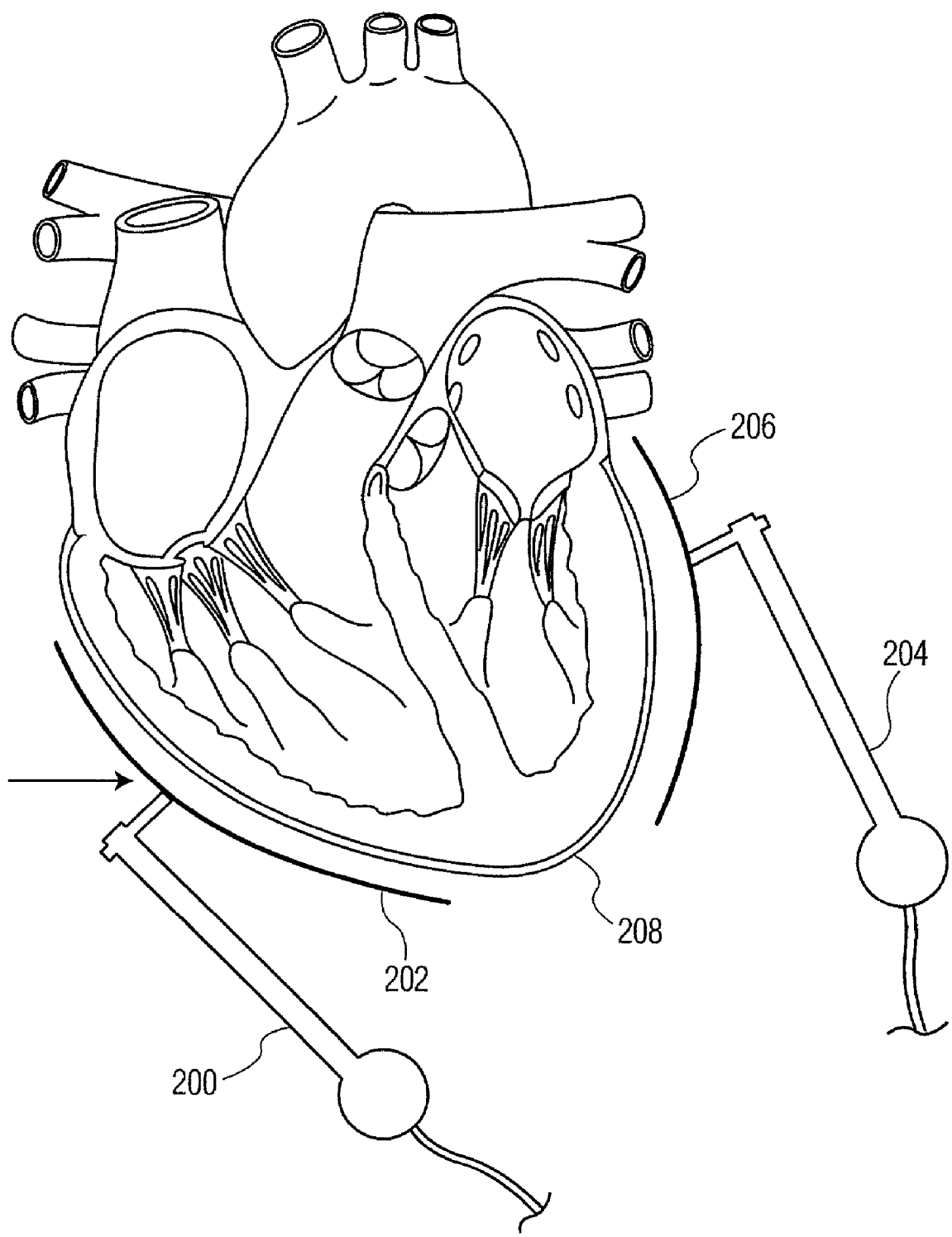
FIG. 2 is a drawing illustrating disposable paddles, according to one embodiment of the present invention.

FIG. 2 is a drawing illustrating disposable paddles, according to one embodiment of the present invention. A first shaft 200 is connected to a first spoon electrode 202. Note that the first shaft 200 has an optional first angle or bend at its distal end which attaches to the first spoon electrode 202 as indicated by the arrow, to facilitate placement of the first spoon electrode 202 on the heart 208. The first spoon electrode 202 is pressed against the heart 208, to make electrical contact. A second shaft 204 is connected to a second spoon electrode 206. Note that the second shaft 204 also has an optional second angle or bend at the distal end. The second spoon electrode 206 is pressed against the heart 208 to make electrical contact. When an electric charge is placed between the first spoon electrode 202 and the second spoon electrode 206, a stopped heart may hopefully start beating again.

The spoon electrodes 202, 206 and/or shafts 200, 204 can be made of a malleable material. This is advantageous, in that each patient's heart is shaped differently, the spoon and/or shaft can be molded by the physician to match the contour of a particular patient's heart. This results in improved electrical contact with the heart.

Figure 3:
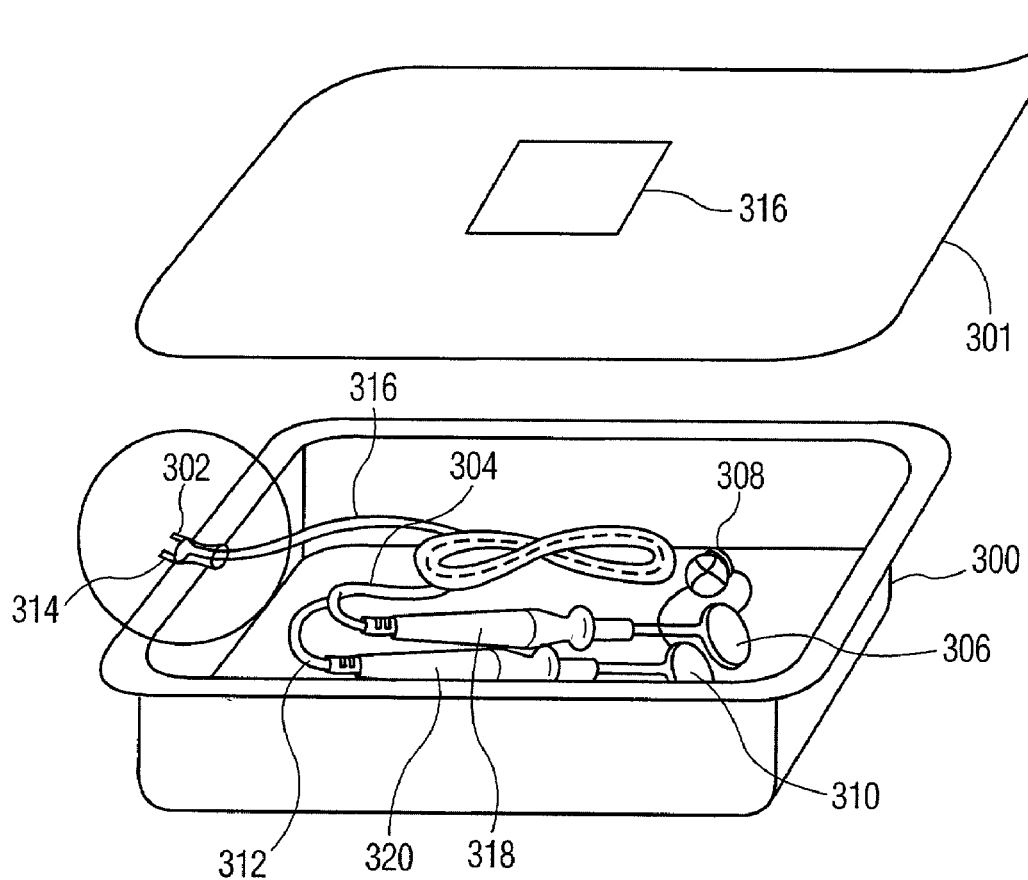
FIG. 3 is a drawing illustrating a package comprising disposable paddles, according to one embodiment of the present invention.

FIG. 3 is a drawing illustrating a package comprising disposable paddles, according to one embodiment of the present invention. A package 300 can be a shallow tray and is typically packaged to maintain the sterility of the contents inside, and is sealed with a lid 301. The lid 301 can be airtight to maintain the sterility of the package 300.

A first connector 302 is located outside of the package 300. The first connector 302 is electrically connected through the package 300 to a first wire 304 located inside the package 300. The first wire 304 is electrically connected to a first spoon electrode 306. The first spoon electrode 306 is electrically connected to a testing unit 308 (to be described in more detail below). The testing unit 308 is electrically connected to a second spoon electrode 310. The second spoon electrode 310 is electrically connected to a second wire 312. The second wire 312 is electrically connected through the package 300 to a second connector 314 located outside of the package 300. Note that the first wire 304 and the second wire 312 can be joined into twin wires 316 in certain places, however the first wire 304 and the second wire 312 are still insulated from each other.

A first handle 318 is attached to the first spoon electrode 306, and a second handle 320 is attached to the second spoon electrode 310. The handles 318, 320, are used by a physician to place the electrode spoons on the patient's heart. In one embodiment of the present invention, the first wire 304 runs through the first handle 318 to the first spoon electrode 306, the first handle 318 being made of a non-conducting material so a physician touching the first handle 318 will not affect the flow of current. The second handle 320 is configured similarly. The handles 318,320 are typically integrally attached to the spoon electrodes 306, 310, respectively.

As a result of the above described configuration, when an electric current is placed between the first connector 302 and the second connector 314, which are both located outside of the package (or on an outside surface of the package), the current can flow inside the package through the testing unit 308.

The testing unit 308 is an electrical device which gives a visual or audible indication that the current applied to the first connector 302 and the second connector 314 flows properly between the spoons.

The testing unit 308 can be, for example, a type of lamp such as a neon lamp, a light emitting diode. The package 300 can contain a clear portion 316 allowing a person to see that the lamp actually lights. In another embodiment, the lid 301 itself can be transparent, so the separate clear portion 316 is not necessary. The testing unit 308 can also be an audible alarm, such as a bell or a buzzer. In this case, the clear portion 316 will typically not be necessary.

Figure 4:
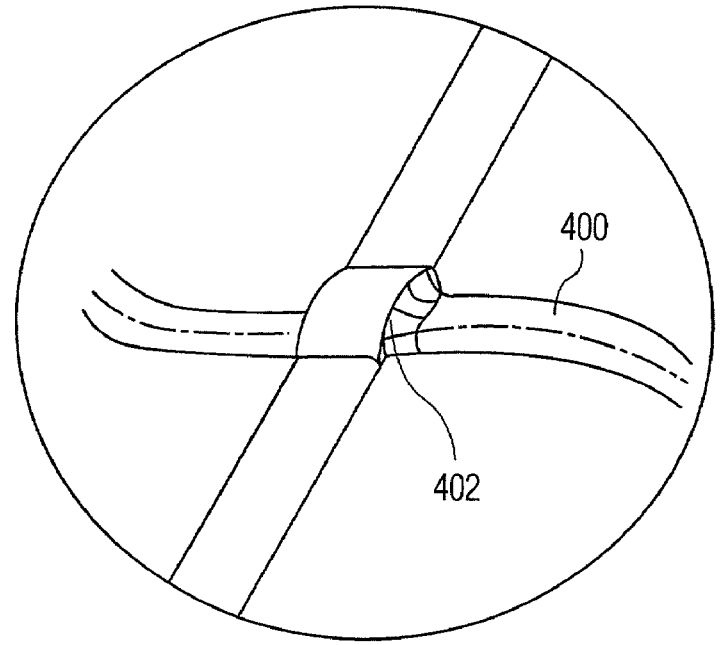
FIG. 4 is a an exploded view of the circled portion of FIG. 3, illustrating bacteria proof seal around cables, according to one embodiment of the present invention.

FIG. 4 is a an exploded view of the circled portion of FIG. 3, illustrating bacteria proof seal (or microbial barrier) around cables, according to one embodiment of the present invention. The twin wires 400 pass through a donut 402 around the twin wires that fuses when the lid of the package (not pictured) is sealed, providing a bacteria proof seal.

Figure 5:
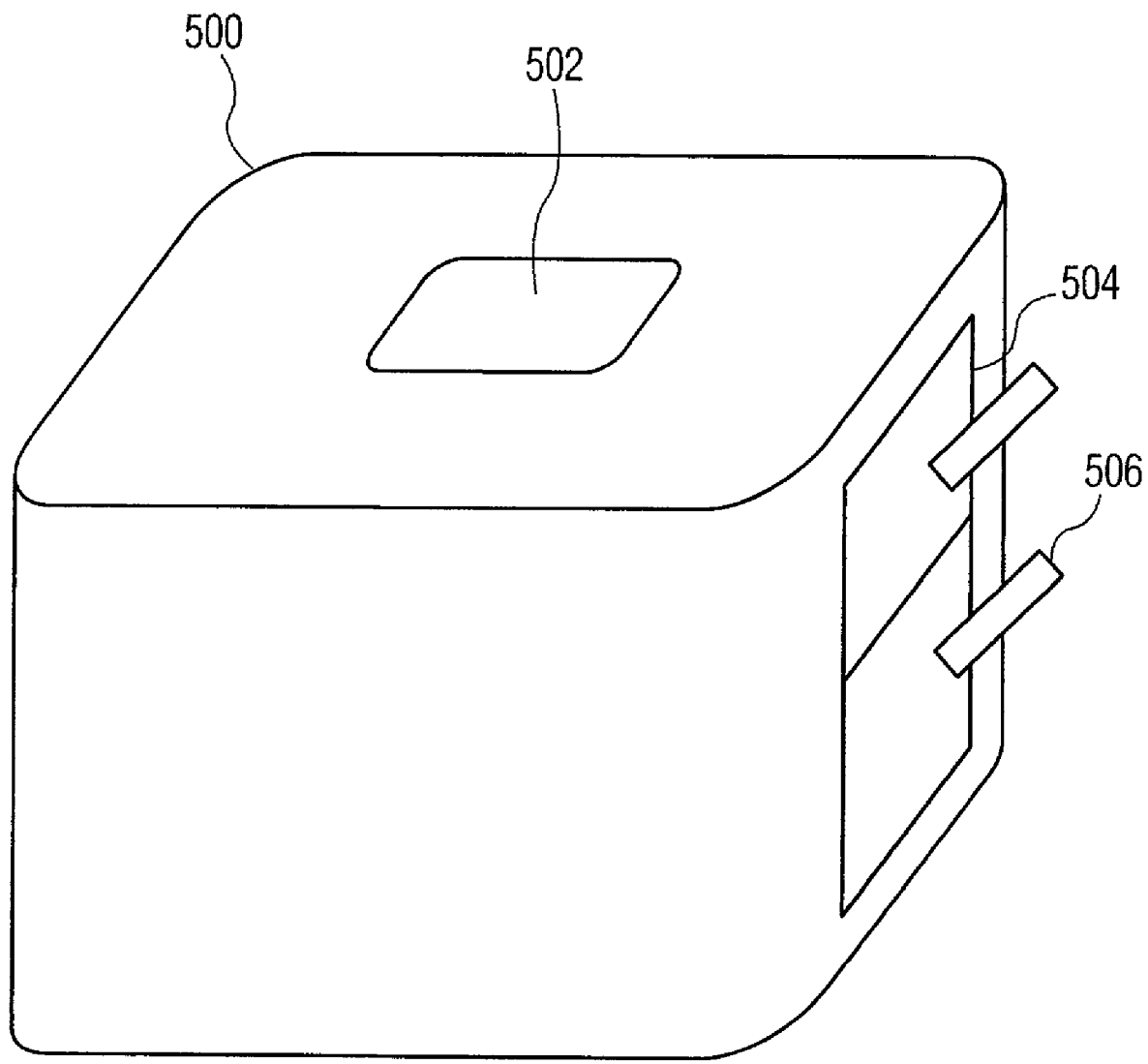
FIG. 5 is a drawing illustrating a self testing package, one embodiment of the present invention.

FIG. 5 is a drawing illustrating a self testing package, one embodiment of the present invention. The package 500 comprises a transparent portion 502 (or visual indicator), so someone can see the contents inside without opening the package. A first clip 504 (or contact) and a second clip 506 are outside the package and can receive an electric charge from a power source (not pictured) by attaching wires from the power source onto the clips.

Figure 6A:
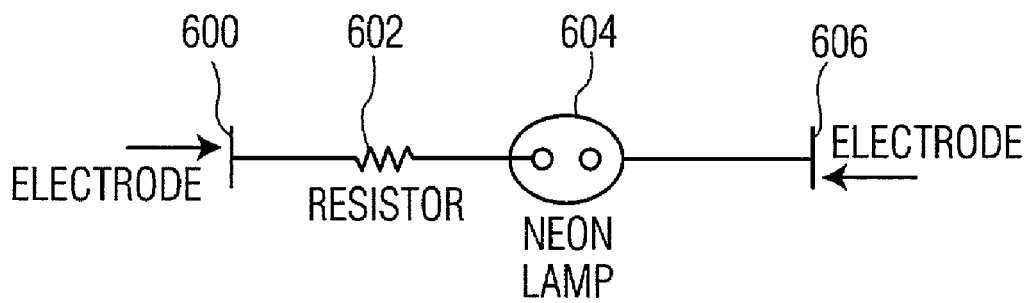
FIGS. 6A, 6B, 6C are circuit diagrams illustrating a testing unit, according to numerous embodiments of the present invention.
Figure 6B:
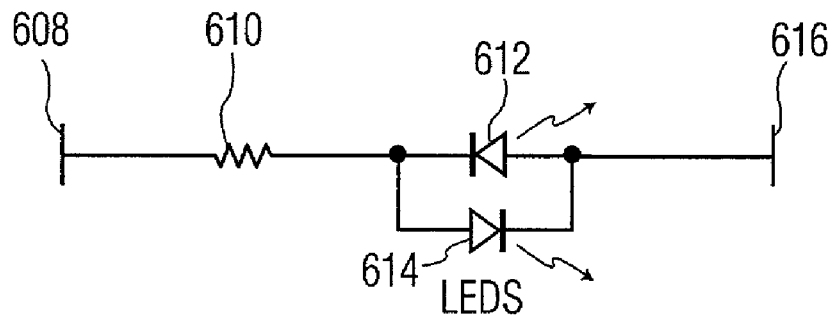
Figure 6C:
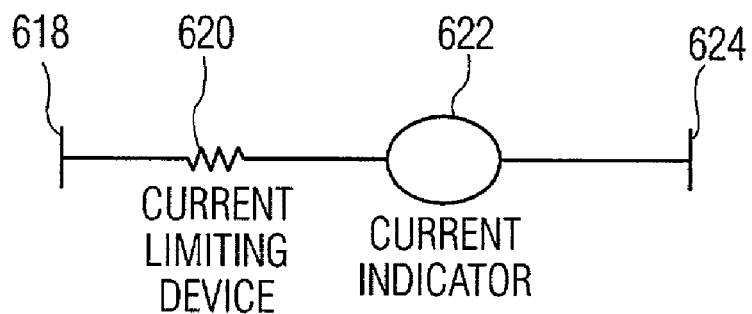

FIGS. 6A, 6B, 6C are circuit diagrams illustrating a testing unit, according to numerous embodiments of the present invention.

Referring now to FIG. 6A, a first electrode 600 is connected to a load resistor 602, which is connected to a neon lamp 604, which is connected to a second electrode 606. When an electric current passes between the first electrode and the second electrode, the neon lamp lights up, indicating a positive test result.

Referring now to FIG. 6B, a first electrode 608 is connected to a load resistor 610 which is connected to a first light emitting diode 612 and a second light emitting diode 614, connected in parallel, which is then connected to a second electrode 616. When an electric current passes between the first electrode 608 and the second electrode 616, the light emitting diodes 612, 614 light up, indicating a positive test result.

Referring now to FIG. 6C, a first electrode 618 is connected to a resistor 620 (or current limiting device), which is connected to a current indicator 622, which is connected to a second electrode 624. When an electric current passes between the first electrode 618 and the second electrode 624, the current indicator 622 activates, indicating a positive test result.

Further, the testing unit can optionally contain a convention voltage checking device, checking for a predetermined voltage before the indicator activates. In this way, if corrosion or other defect results in a smaller voltage than applied, this will identify the problem. An optional switch can also be connected to testing unit to allow a user to operate the unit by pressing a switch assuming everything is connected properly.

It can be appreciated that one of ordinary skill in the art can modify the above circuits illustrated in FIGS. 6A, 6B, and 6C, resulting in various configurations designed to give an indication (visual, audible, or otherwise) that the current is flowing properly through the two electrodes.

Spoon electrodes can be made of a malleable conductive material, so that a physician can mold the spoon electrode to a particular shape matching the patient's heart. Because prior art non-disposable spoons were designed to last over a large number of uses, they were typically made of a rigid thick material, which could not be shaped. The present invention spoon electrodes can be made of, for example, a thin aluminum alloy or stainless steel. Since these spoon electrodes are disposable, there is no concern over bending the material too much that the spoon may not last for the next use. Further, the shaft can also be made of a malleable nonconductive material, so that a physician can mold the shaft to better accommodate the heart. The shaft can be made of a malleable nonconductive material, such as molded rubber or plastic.

The package containing the disposable paddles will typically be sterile, so that a surgeon need not worry about sterilizing the paddles once he needs them. The sterilization of the contents of the package can be typically performed by any one of a number of known sterilization methods, such as, for example, using gamma radiation or ethylene oxide.

Figure 7:
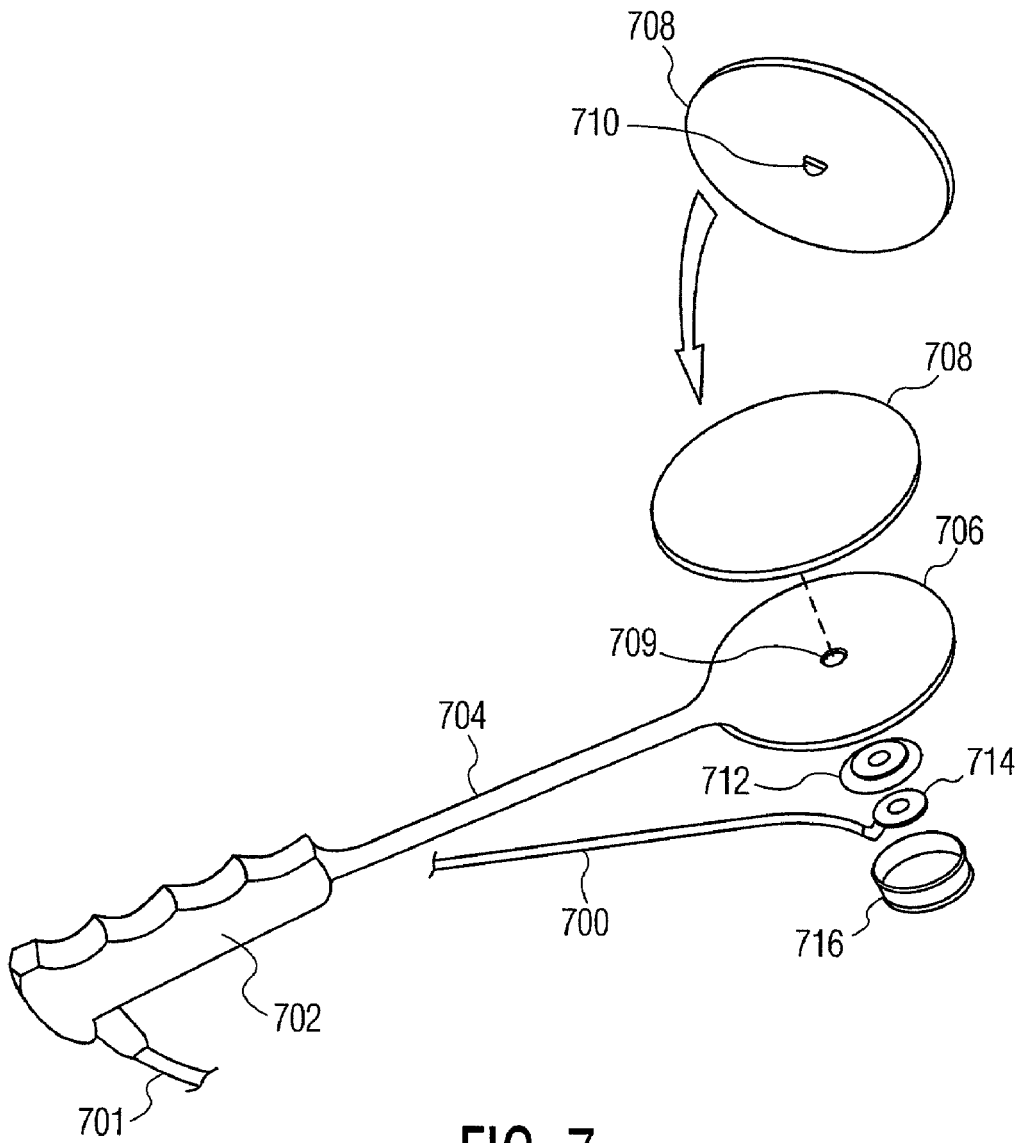
FIGS. 7 and 7A are drawings illustrating a disposable paddle, according to one embodiment of the present invention.
Figure 7A:
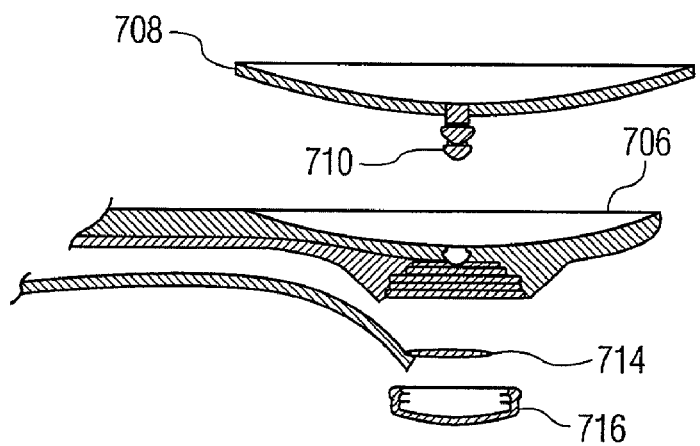

FIG. 7 is a drawing illustrating a disposable paddle, according to an embodiment of the present invention. FIG. 7A is a cross-sectional view of the spoon electrode end of the disposable paddle of FIG. 7.

As stated above, the present invention can provide a disposable one-use paddle assembly, providing a cost efficient and easy system. FIG. 7 illustrates an embodiment of such an assembly.

A wire 701 carrying electric current used to shock a patient's heart is connected to a handle 702. The handle connects to a shaft 704, which connects to a spoon 706. The handle 702, shaft 704, and spoon 706 are typically integrally molded into one piece. The handle 702, shaft 704, and spoon 706, can also be made of any variety of molded plastic. In this embodiment, the handle, shaft, and spoon are made of nonconductive material.

The wire 701 passes directly through the handle 702 and shaft 704 so that the wire 701 is not conductively exposed at any point up to the spoon 706. Alternatively, the wire can be an insulated wire 700, which passes under the handle 702 and shaft 704. The shaft 704 may also comprise a groove (not illustrated) through an underside of the shaft 704 to receive the wire 700.

An electrode plate 708 (or conductive plate) snaps onto the spoon 706, the electrode plate 708 providing an electrical contact to the patient's heart. The electrode plate 708 comprises a head 710, which snaps into a receiving unit 709 (in this case, a hole) in the spoon 706. An optional electrode plate washer 712 snaps onto the head 710 to lock the electrode plate 708 into place on the spoon 706.

A conductive washer 714 is connected to the wire 700 and snaps onto the head 710, electrically connecting the conductive washer 714 to the electrode plate 708. A portion of the head 710 that snaps onto the conductive washer 714 should be made of conductive material so that current can pass to the electrode plate 708.

A cap 716 can be placed over the conductive washer 714 to ensure that the current passing through the conductive washer 714 is not exposed. The cap 716 can be attached over the conductive washer 714 to the spoon 706 by a number of conventional methods, for example an adhesive can be used, or a circular groove (not pictured) can be molded into the spoon 706 so that the cap 716 can snap onto the groove.

Note that in another embodiment, the wire 700 can pass directly through the handle 702 and shaft 704, and connect directly with a conductive middle part of the head 710. In this embodiment, the washers 712 and 714 and cap 716 are not needed, as the wire 700 is not conductively exposed to any outside surface other than the electrode plate 708. Note that in this embodiment, the middle part of the head 710 will be made of conducting material, while a tip of the head 710 will not be made of conducting material.

In another embodiment of the present invention, the handle 702 can comprise an opening (not pictured) to receive the shaft 704. In this way, the effective length of the shaft 704 can be adjusted by sliding the shaft 704 through the handle 702. The shaft can be locked in to the into the handle so it does not slide once it is set to a desired length by any conventional locking mechanism, such as a locking collar.

In another embodiment of the present invention, a paddle can comprise a handle which is integrally attached to a non conducting shaft which is integrally attached to a conductive spoon electrode. Unlike the above embodiment, this paddle is manufactured with a conductive spoon electrode integrally attached to the shaft. In this embodiment, a separate electrode plate (as described above) is not needed. Other than the separate electrode plate, all of the above described embodiments can be applied to this variation of the invention.

Although a few preferred embodiments of the present invention have been shown and described, it would be appreciated by those skilled in the art that changes may be made in this embodiment without departing from the principles and spirit f the invention, the scope of which is defined in the claims and their equivalents.

What is claimed is:

1. An apparatus comprising:
   a handle attached to a shaft attached to a spoon, the spoon having a receiving unit, and the handle, the shaft, and the spoon are all made of nonconducting material; and
   an electrode plate attaching onto the receiving unit of the spoon adapted to be in contact with the heart of a patient.

2. The apparatus as recited in claim 1, wherein the handle and the shaft and the spoon are integratedly molded into one piece.

3. The apparatus as recited in claim 1, further comprising a wire electrically connected to the electrode plate.

4. The apparatus as recited in claim 3, wherein the wire passes through the handle and the shaft.

5. The apparatus as recited in claim 1, wherein the spoon and the electrode plate are both circular.

6. An apparatus as recited in claim 1, wherein the shaft is made of a malleable material.

7. The apparatus as recited in claim 1, wherein the spoon is made of a malleable material.

8. The apparatus as recited in claim 1, wherein the receiving unit comprises a hole in a center of the spoon, and the electrode plate comprises a head in a center of the electrode plate which snaps into the hole.

9. An apparatus as recited in claim 1, wherein the shaft contains a bend.

10. An apparatus as recited in claim 1, wherein the handle comprises an opening receiving the shaft, so that the shaft can adjustably slide into the handle thereby adjusting a length of the shaft.

11. An apparatus as recited in claim 1, wherein the receiving unit allows the electrode plate to snap onto the spoon.

12. An apparatus as recited in claim 1, further comprising:
a sterile package storing the handle, and the shaft, and the spoon electrode in a sterile manner;
a self testing unit electrically connected to the spoon electrode; and
a wire connecting to the spoon electrode, the wire protruding outside the package through a microbial barrier, allowing the self testing unit to operate without opening the package,
wherein the spoon electrode is made of a malleable material,
wherein the shaft is made of a malleable material,
wherein the shaft contains a bend, and
wherein the handle comprises an opening receiving the shaft, so that the shaft can adjustably slide into the handle thereby adjusting a length of the shaft.

13. An apparatus as recited in claim 1, further comprising a sterile package storing the handle, shaft, spoon, and electrode plate, in a sterile manner.

14. An apparatus as recited in claim 13, further comprising a self testing unit.

15. An apparatus as recited in claim 14, further comprising a wire connecting to the electrode plate which protrudes outside the package through a microbial barrier, allowing the self testing unit to operate without opening the package.

16. An apparatus comprising:
a handle attached to a shaft attached to a spoon, the spoon having a receiving unit, and the handle, and the shaft, and the spoon are all made of nonconducting material;
an electrode plate attaching onto the receiving unit of the spoon adapted to be in contact with the heart of a patient,
a sterile package storing the handle, and the shaft, and the spoon, and the electrode plate, in a sterile manner;
a self testing unit; and
a wire connecting to the electrode plate which protrudes outside the package through a microbial barrier, allowing the self testing unit to operate without opening the package,
wherein the handle and the shaft and the spoon are integratedly molded into one piece,
wherein the wire passes through the handle and shaft,
wherein the spoon and electrode plate are both circular,
wherein the shaft is made of a malleable material,
wherein the spoon is made of a malleable material,
wherein the shaft contains a bend,
wherein the handle comprises an opening receiving the shaft, so that the shaft can adjustably slide into the handle thereby adjusting a length of the shaft,
wherein the receiving unit comprises a hole in a center of the spoon, and the electrode plate comprises a head in a center of the electrode plate which snaps into the hole, and
wherein the receiving unit allows the electrode plate to snap onto the spoon.

17. An apparatus as recited in claim 16, wherein the spoon electrode is made of a malleable material.

18. An apparatus as recited in claim 17, wherein the shaft is made of a malleable material.

19. An apparatus as recited in claim 17, wherein the shaft contains a bend.

20. An apparatus as recited in claim 17, wherein the handle comprises an opening receiving the shaft, so that the shaft can adjustably slide into the handle thereby adjusting a length of the shaft.

21. An apparatus as recited in claim 17, further comprising a sterile package storing the handle, and the shaft, and the spoon electrode in a sterile manner.

22. An apparatus as recited in claim 21, further comprising a self testing unit electrically connected to the spoon electrode.

23. An apparatus as recited in claim 22, further comprising a wire connecting to the spoon electrode, the wire protruding outside the package through a microbial barrier, allowing the self testing unit to operate without opening the package.

* * * * *